United States Patent [19]

Miller et al.

[11] 4,055,168
[45] Oct. 25, 1977

[54] POSTURE TRAINING DEVICE

[75] Inventors: Neal E. Miller; Barry R. Dworkin, both of New York, N.Y.

[73] Assignee: The Rockefeller University, New York, N.Y.

[21] Appl. No.: 725,231

[22] Filed: Sept. 21, 1976

[51] Int. Cl.² ............................................. A61B 5/00
[52] U.S. Cl. .................................... 128/2 S; 128/78; 340/279
[58] Field of Search .................. 128/2 S, 78; 340/279, 340/283; 2/44, 45

[56] References Cited

U.S. PATENT DOCUMENTS 4,007,733   2/1977   Celeste et al. ........................ 128/2 S

*Primary Examiner*—John D. Yasko
*Attorney, Agent, or Firm*—Oblon, Fisher, Spivak, McClelland & Maier

[57] ABSTRACT

A posture training device includes in a mechanical-electrical embodiment thereof, an electrically conductive plate divided into two contact zones and slidable upon a support base of one housing section of the device. One end of the plate is operatively connected to a body harness cable extending around the longitudinal axis of the body from the pubis to the scapula, while the other end of the plate is electrically connected to spring-biased cable winding mechanisms. The two zones of the plate are separated and electrically insulated from each other by a predetermined gap which extends along the plate with a predetermined curvature or rectilinearly at a constant slope, and another slidable plate, having a contact member disposed therein, is similarly provided within another housing section with a harness cable at one end thereof, which cable extends laterally about the chest area of the patient, and is operatively, electrically connected to a spring-biased cable winding mechanism at the other end thereof through means of the contact member. The electricaly conductive plate and contact member of the second plate serve as a single-pole, double-throw switch and common contact member respectively, and the relative movement of both plates, as defined by the contact member and the zones of the electrically conductive plate, serve to open or close a signal emitting circuit so as to accurately indicate the assumption of a proper or improper postural position or condition by the patient, independent of the respiration of the patient.

In another, electronic embodiment of the invention, in lieu of the sliding plates of the aforenoted embodiment, rotary potentiometers are utilized, the generated voltages of which serve to indicate the length or lengthening, or movement, of the cables secured thereto in a manner similar to the securing of the same to the sliding plates, and through means of a trim resistor, which serves a similar function as that of the sloped gap of the zoned plate, the voltages are differentially and then comparatively amplified and supplied to the signal emitting circuit.

15 Claims, 6 Drawing Figures

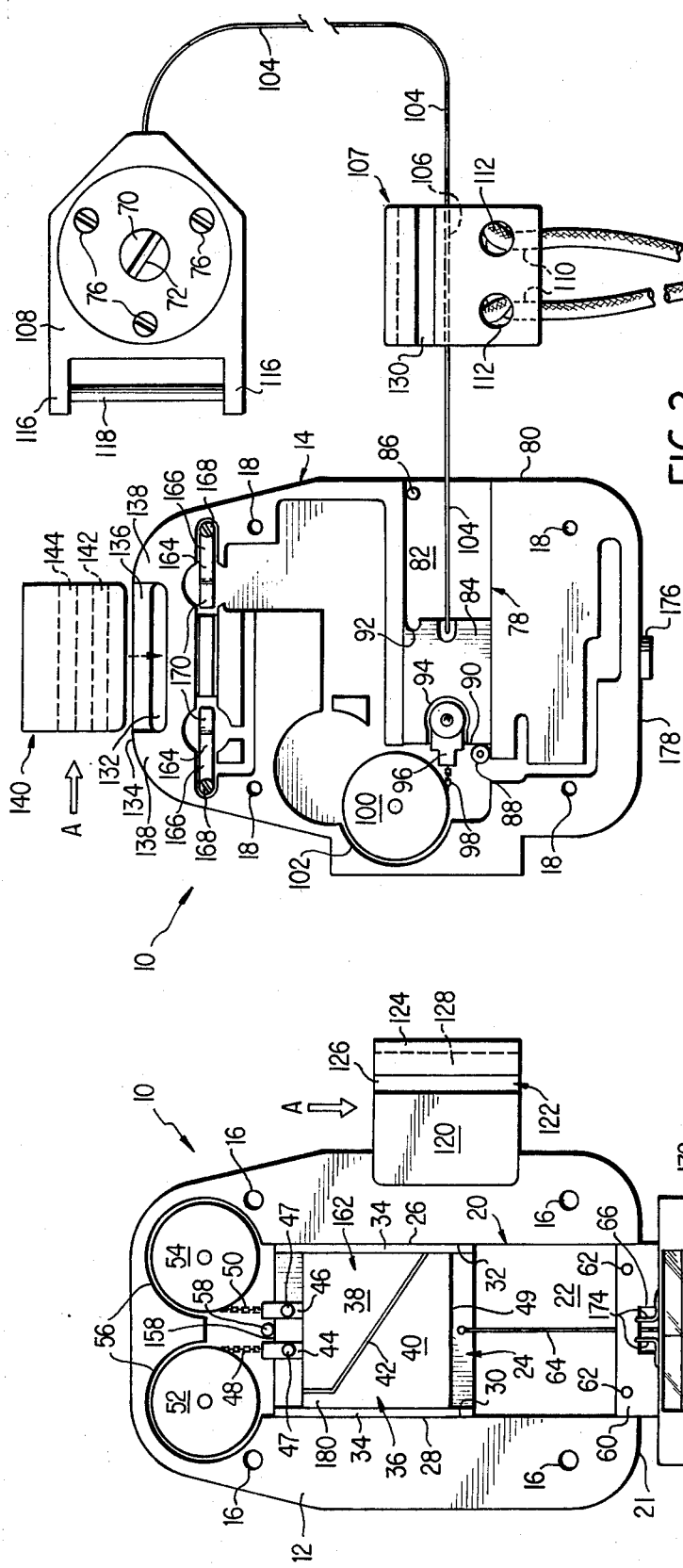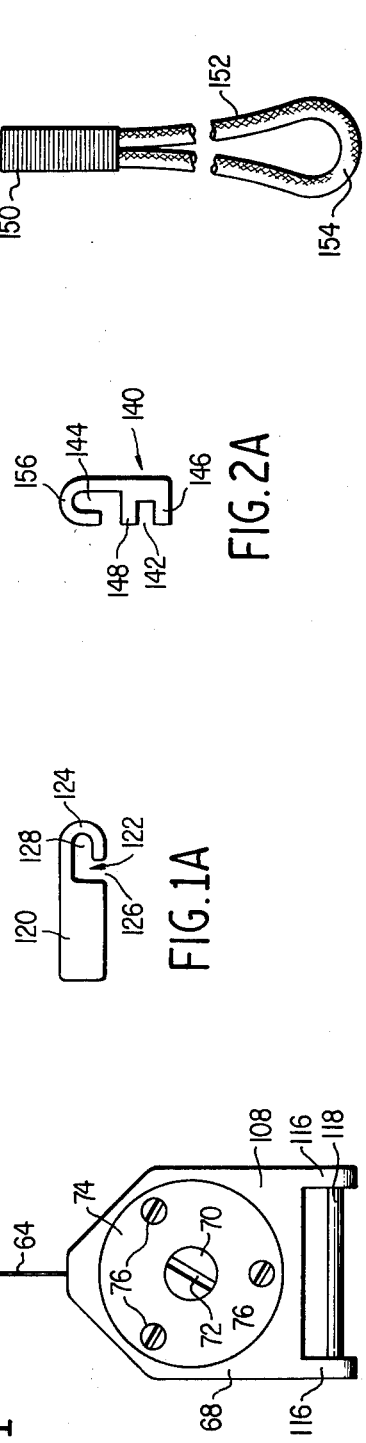

POSTURE TRAINING DEVICE

The present invention was wholly or partially made with funds provided by the Department of Health, Education and Welfare. Accordingly, the U.S. Government has a royalty free license under any patent granted with respect to this invention.

BACKGROUND OF THE INVENTION

1. Field to the Invention

The present invention relates generally to training devices for the treatment of idiopathic diseases, and more particularly to a posture-training device for the treatment of idopathic scoliosis.

2. Description of the Prior Art

In treating scoliosis, various prior art devices have been devised in an attempt to physically force the patient into attaining a good postural position, however, such devices have enjoyed only limited use as the same have obvious operational disadvantages, such as, for example, the fact that they are uncomfortable to wear, and are often in the form of a harness, brace or the like, which have little or no resiliency and are, in fact, quite confining and restrictive.

Other prior art devices have comprised belt-type implements to be worn by the patient about the abdominal area, which, in effect, monitor the tautness, and concomitantly the relaxation or distension, of the abdominal muscles, however, such devices have also enjoyed only a limited use due to the fact that the same only serve to indirectly correct the postural state of the patient, and in addition, are quite taxing on the patient's fortitude for, in fact, maintaining the contracted state of his or her abdominal muscles.

Still other prior art devices have comprised harness type implements which have one or more elongated, flexible members disposed substantially along the patient's back so as to be juxtaposed to the spinal column, and an alarm, tone, or vibration emitting device operatively connected thereto. Upon a change in length of the flexible members, which would allegedly indicate a deviation in posture of the patient from the desired, predetermined or preset state, the alarm, tone, or vibrator is actuated alerting the patient to the fact that an incorrect postural position has been assumed. The operational disadvantage of these devices, however, has been the heretofore unrecognized fact that the patient's respiration affects the length of such flexible members, and therefore, the devices do not truly reflect the assumption, by the patient, of a correct or incorrect postural state.

More particularly, within one such device of the latter type of devices, a single flexible member is disposed solely along the patient's back within the area defined by the spinal column, and as the patient's posture changes from one of good posture to one of poor posture, the flexible member, which may be, for example, an extensible cable, lengthens so as to actuate the electrical circuitry operatively associated with the tone, alarm, or vibrator elements. However, as a change in length may also be sensed as a result of the patient's respiration, that is, the expansion of the upper torso affects the body harness supporting the flexible members, the flexible members will likewise be affected and lengthened such that an erroneous detection of allegedly poor posture will be detected as a result of such respiration.

Similarly, within another device of the particular aforenoted type of devices, a flexible member or cable may be similarly disposed upon the patient's body, but in fact extends completely around the torso, in the longitudinal direction thereof, and upon both the anterior and dorsal sides thereof, the cable being supported upon the patient's body at the scapulae and pubis. In such an arrangement, when the patient assumes the correct postural position, the length of the flexible member will be substantially maximized, while when an incorrect postural position is assumed, the length of the member will be correspondingly decreased, due to the slouching of the person and the overall contraction of the body length, and the alarm, tone, or vibrator element will be actuated. However, as the expansion of the chest cavity affects the length of the flexible member, a contraction of the same due to the assumption of a poor postural position can be offset by the respiration of the patient which will somewhat extend the member or cable, and consequently, accurate detection of a poor postural position or condition cannot be readily detected.

In summary, the defects or disadvantages of the prior art can be characterized by the fact that none of such devices effectively deal with or monitor the underlying curvature of the patient and/or treat the same in a physically therapeutic corrective manner.

SUMMARY OF THE INVENTION

Accordingly, it is an object of the present invention to provide a new and improved posture training device.

Another object of the present invention is to provide a new and improved posture training device which overcomes the problems of prior art devices.

Still another object of the present invention is to provide a new and improved posture training device which accurately detects the assumption of a poor postural position by a patient.

Yet another object of the present invention is to provide a new and improved posture training device the operation of which accommodates normal movement of the patient.

Yet still another object of the present invention is to provide a new and improved posture training device which does not physically confine or restrict the normal movements of the patient.

Still yet another object of the present invention is to provide a new and improved posture training device which is directly operatively associated with that portion of the patient's body which determines the postural position or condition of the same.

A further object of the present invention is to provide a new and improved posture training device the operation of which is not adversely affected by normal movements of the patient or normal body functions.

A still further object of the present invention is to provide a new and improved posture training device which issues one or more tone signals indicating to the patient that an incorrect postural position or condition has been assumed.

A yet further object of the present invention is to provide a new and improved posture training device which issues a tone signal loud enough to be heard by others, after an initial tone signal is emitted which is only audible to the patient, so as to motivate the patient to be alert to the tone signals and thereby immediately assume a correct posture before the emission of the second tone signal and preferably to retain such position or condition such that none of the signals will be emitted.

A yet still further object of the present invention is to provide a new and improved posture training device which effectively deals with, monitors, and/or treats, in a physically therapeutic corrective manner, the underlying curvature of the patient's spinal column.

The foregoing and other objects are achieved in accordance with the present invention through the provision of a posture training device which includes in a mechanical-electrical embodiment thereof, an electrically conductive plate divided into two contact zones and slidable upon a support base of one housing section of the device. One end of the plate is operatively connected to a body harness cable extending around the longitudinal axis of the body from the pubis to the scapula, while the other end of the plate is electrically connected to spring-biased cable winding mechanisms. The two zones of the plate are separated and electrically insulated from each other by a predetermined gap which extends along the plate with a predetermined curvature or rectilinearly at a constant slope, and another slidable plate, having a contact member disposed therein, is similarly provided within another housing section with a harness cable at one end thereof, which cable extends laterally about the chest area of the patient, and is operatively, electrically connected to a spring-biased cable winding mechanism at the other end thereof through means of the contact member. The electrically conductive plate and contact member of the second plate serve as a single-pole, double-throw switch and common contact member respectively, and the relative movement of both plates, as defined by the contact member and the zones of the electrically conductive plate, serve to open or close a signal emitting circuit so as to accurately indicate the assumption of a proper or improper postural position or condition by the patient, independent of the respiration of the patient.

In another, electronic embodiment of the invention, in lieu of the sliding plates of the aforenoted embodiment, rotary potentiometers are utilized, the generated voltages of which serve to indicate the length or lengthening, or movement, of the cables secured thereto in a manner similar to the securing of the same to the sliding plates, and through means of a trim resistor, which serves a similar function as that of the sloped gap of the zoned plate, the voltages are differentially and then comparatively amplified and supplied to the signal emitting circuit.

BRIEF DESCRIPTION OF THE DRAWINGS

Various other objects, features, and attendant advantages of the present invention will be more fully appreciated as the same becomes better understood from the following detailed description when considered in connection with the accompanying drawings, in which like reference characters designate like or corresponding parts throughout the several views, and wherein:

FIG. 1 is a front elevation view of the rear half or housing section of one embodiment of a posture training device constructed in accordance with the present invention and showing its cooperative parts;

FIG. 1A is a plan view of a hook-type clasp or catch operatively connected to the housing section of FIG. 1 as viewed in the direction of arrow A of FIG. 1;

FIG. 2 is a rear elevation view of the front half or housing of a posture training device constructed in accordance with the present invention and showing its cooperative parts, such front half being adapted to be operatively engaged with the rear half shown in FIG. 1;

FIG. 2A is a side elevation view of a hook-type clasp or catch operatively associated with the housing section of FIG. 2 as viewed in the direction of arrow A of FIG. 2.

DETAILED DESCRIPTION OF THE ILLUSTRATED EMBODIMENTS

Figure 3:
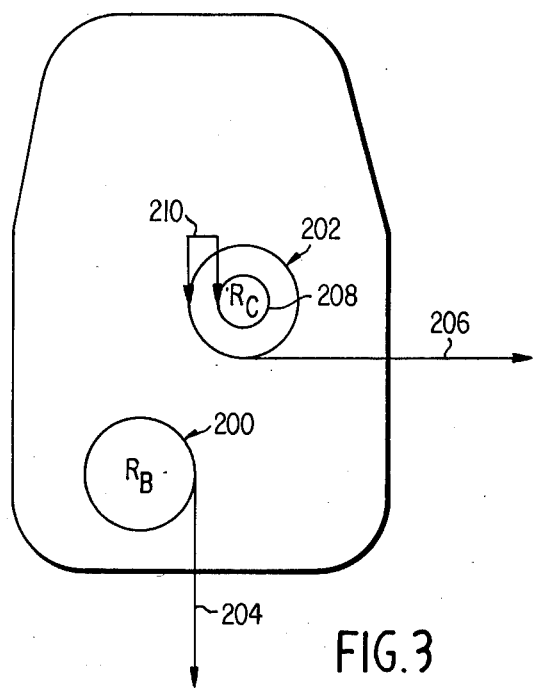
FIG. 3 is a schematic view of another embodiment of a posture training device constructed in accordance with the present invention.

Referring now to the drawings, and more particularly to FIGS. 1 and 2 thereof, a first embodiment of the present invention is generally indicated at 10 and is seen to include rear and forward housing sections 12 and 14, respectively, which are adapted to be mated together by means of suitable threaded fasteners, not shown, which are to be inserted within threaded bores 16 and 18, respectively provided within or near the corner portions of the housings 12 and 14.

The front face of housing 12 is provided with a rectangular recessed portion 20, the longitudinal axis of which corresponds with the longitudinal axis of the housing 12, however, although the recess 20 commences at the lower or bottom surface 21 of the housing 12, the same does not extend the full height of the housing 12. The recessed portion 20 serves to define a support base 22 upon which a rectangular support plate 24 is slidably disposed, the housing section 12, as well as plate 24, being made of a suitable plastic material whereby the sliding engagement between plate 24 and base 22 is essentially frictionless, or in other words, the friction generated thereby is negligible. In order to retain plate 24 within recess 20, the lateral mating edges 26 and 32, and 28 and 30, of the recess 20 and plate 24, respectively, are beveled laterally outwardly somewhat analogous to a rabbet groove, not shown.

Plate 24 is provided with longitudinally extending ridges 34 disposed along the lateral edges thereof, and an essentially square electrical contact plate 36 is fixedly secured thereon, the mating lateral edges of plate 36 and ridges 34 being configured similarly to the beveled configurations of the mating edges of plate 24 and recessed portion 20 so as to maintain plate 36 supported upon plate 24. Plate 36 is fabricated from a nylon base material which is then coated or laminated with an electrically conductive surface, such as, for example, gold foil, and is divided into two essentially triangular, complementary sections, an upper section 38 and a lower section 40, which are separated and insulated from each other by means of a thin gap 42 which extends downwardly from substantially the upper left corner of plate 36 to the lower right corner thereof in accordance with a predetermined curvature, or rectilinearly at a constant slope or angle of approximately 35°, with respect to a horizontal plane, such being reflective or corresponding to a person's respiration, as will be more fully apparent hereinafter. In this manner, two separate electrical contact areas are defined by sections 38 and 40.

Electrical contact terminal members 44 and 46 are fixed to plate 24 by suitable means, such as, for example, fasteners 47, and are respectively connected to the sections 38 and 40, in a suitable manner, such as, for example, contact member 44 is directly soldered to electrical section 38 while contact member 46 is extended beneath sections 38 and 40, the rear faces of which are not electrically coated, and soldered to the section 40 at the lower edge 49 thereof. In this manner, the soldered connections also serve to define the longitudinal position of plate 36 with respect to plate 24 and to maintain the same so fixed.

Contact members 44 and 46 are likwise connected to metal chains or cables 48 and 50 which are respectively disposed about reels 52 and 54 which are rotatably supported within substantially circular recessed portions 56 of housing 12 and which are biased, respectively, in the counterclockwise and clockwise directions by watch-spring mechanisms, not shown, so as to normally dispose plates 24 and 36 in the position shown in FIG. 1. The watch springs are approximately (20inches) in length and are isotonic, that is, the spring force or tension transmitted to the chains 48 and 50, and to the sliding plate assembly, is essentially constant, or in other words, independent of the displacement of the chains or cables. In addition, it is to be additionally noted that the chains or cables are fabricated of silver, for it has been found that other metal cables, such as, for example, those fabricated of stainless steel, have exhibited metal fatigue and have crystallized after a relatively short period of time of operation, which of course renders the device inoperative.

In order to determine or define the limits of the longitudinal movements of the plate assembly 24-36 relative to recessed portion 20 and upon support base 22, an upper stop member 58, comprising a small, cylindrical metal rod, is disposed along the centerline of the housing 12 at a longitudinal position thereof which in effect defines the upper extent of recessed portion 20 so that the same is interposed between chains 48 and 50, as well as contact members 44 and 46. Similarly, a mounting plate 60, having a substantially inverted U-shaped configuration, has its upper portion disposed within the lower extent of recessed portion 20 and is in fact fixedly secured to base 22 by means of fasteners 62. It will thus be appreciated that as the depth of plate 60 is equal to that of recessed portion 20, and similarly for the depth or height of stop 58, which depths are greater than that of plate 24, the longitudinal movement of plate 24, and therefore plate 36, is limited by stop 58 and plate 60, however, the latter members do not interfere with the mated fitting of housings 12 and 14 as the same do not protrude upwardly or forwardly beyond the surface of housing 12. This is likewise true of the depth of the plate assembly 24-36, that is, the contact surface of plate 36 lies flush or within the same plane as that of the surface of housing section 12.

A harness cable 64 is fixedly secured at one end thereof to the lower portion of plate 24 at a position along the longitudinal centerline thereof and is seen to extend downwardly through a bore, not shown, provided within plate 60 and to extend outwardly through the slot 66 defined by U-shaped plate 60. The other end of cable 64 is adjustably secured within a harness cable housing 68 having a configuration somewhat similar to housing sections 12 and 14, and within which is disposed a rotatable reel, not shown, about which cable 64 is coiled, and which is operatively connected to a rotatable projection 70 having a slot 72 defined therein within which a tool, such as, for example, a screwdriver, may be inserted for rotating the same.

A circular pressure plate 74 is disposed within a similarly configured recess of housing 68, within which the reel is also disposed, so as to cover the reel, and the plate 74 is removably secured to housing 68 by means of a plurality of threaded fasteners 76. In order to adjust the length of cable 64, fasteners 76 are loosened and projection 70 rotated in the proper direction for either lengthening or shortening the cable. Upon completion of the adjustment, fasteners 76 are tightened so as to bring pressure plate 74 into contact with the cable reel and the coiled cable disposed interiorly of housing 68, whereupon further rotational adjustment of the reel and cable is prevented. In order to facilitate wear resistance of the cable, as well as essentially frictionless contact with the patient's body during operational periods, cable 64 actually comprises a smooth nylon strand encased within a small Teflon tube or sheath and is freely movable therethrough, such materials also being skin acceptable.

Considering more particularly housing section 14, a rectangular recessed portion 78, similar to recessed portion 20 of housing section 12, is defined within section 14 so as to be horizontally disposed therein, the recess 78 commencing at the right edge surface 80 of housing 14 and extending leftwardly, as seen in FIG. 2, however, the same does not extend the full width of the housing. Recess 78 serves to define a support base 82 upon which a rectangular support plate 84 is slidably disposed, the housing section 14 and plate 84 being fabricated of the same plastic material as that of housing section 12 and plate 24 so as to similarly facilitate the essentially frictionless sliding engagement between support base 82 and plate 84.

In order to retain plate 84 within recess 78, the upper and lower mating edges thereof are beveled in a similar manner as are those of recess 20 and plate 24, and in order to further define the travel limits or stroke of plate 84, a metal stop member 86, similar to stop member 58, is disposed within the upper right corner of recess 78, as viewed in FIG. 2, while a similar stop member 88, made of, for example, plastic or rubber, is disposed in the lower, left corner of recess 78. Stop member 88 is seen to merely engage the left, lateral, flat or planar surface 90 of plate 84 in order to limit the travel thereof, however, the upper right corner of plate 84 may be provided with a semi-circular cut-out portion 92 which is adapted to matingly engage stopper member 86.

Plate 84 is further provided, within the left side portion thereof, with a substantially circular recessed portion 94 within which an electrical contact terminal 96 is disposed, and in a manner similar to contact terminals 44 and 46, terminal 96 is electrically connected to a metal chain or cable 98, which may likewise be made of silver and which is, in turn, disposed about a reel 100 which is rotatably supported within another semi-circular recessed portion 102 of housing 13. Reel 100 is biased in the clockwise direction, as viewed in FIG. 2, by means of a watch-spring mechanism which is similar to the mechanism operatively associated with reels 52 and 54, and consequently, plate 84 is normally disposed against stopper member 88.

A harness cable 104 is fixedly secured at one end thereof to the right side portion of plate 84, as viewed in FIG. 2, at a position disposed along the longitudinal centerline of plate 84, as is contact member 96, while the other end of cable 104 is freely disposed through a through-bore 106 defined within a substantially square or rectangular housing 107 and is adjustably secured within a harness cable housing 108 which is identical to housing 68. Housing 107 is further provided with two bores 110, which extend within a plane disposed parallel to the rear or front surfaces of housing 107 and which are disposed perpendicularly with respect to through-bore 106, as well as with two additional bores 112 which extend perpendicular to the front or rear surface of the housing 107 and which communicate with bores 110. In this manner, the free ends of a non-elastic harness 114 may be secured within housing 107.

Referring again to FIG. 1, it will also be seen that cable housing 68 is further provided with a pair of dependent ears 116 between which is fixedly secured a clasp or catch bar 118, and as noted hereinabove, as housing 108 is identical to housing 68, such catch or clasp structure is likewise provided upon housing 108. Housing 12 is also integrally provided with a catch or clasp housing 120 which is adapted to mate with housing 108, and more particularly, it is seen that housing 120, as best seen from FIGS. 1 and 1A, has a substantially L-shaped slot 122 defined therein.

It will be further appreciated that the lateral distance defined between ears 116 of the cable housing 108 is somewhat greater than the width of housing 120, as is the length of catch bar 118, while the diameter of bar 118, as seen in cross-section, is somewhat similar than the corresponding dimension of slot 122 so at to permit the same to be inserted therein while simultaneously permitting the hooked outer portion 124 of housing 120 to be disposed within the space defined between catch bar 118 and the main body portion of cable housing 108. In order to mate housings 108 and 120, it will be readily perceivable that catch bar 118 will initially be disposed or inserted within the open leg portion 126 of slot 122 and upon mating together of the housings, the bar 118 may then be moved into the locking leg portion 128 of slot 122 whereby the two housings will in fact be removably locked together. Housing 107 is similarly provided with an L-shaped slot 130 within the lower portion thereof and the same is adapted to be mated with cable housing 68 in precisely the same manner as housings 108 and 120 are mated.

Referring again to FIG. 2, the upper central portion of housing 14 is provided with a laterally extending through-slot 132 within the vicinity of the upper edge 134 of the housing, and a bridging bar 136, having a depth or thickness of approximately only one-half that of the housing 14 is integrally formed with and interposed between upwardly projecting ear portions 138 in a manner somewhat analogous to the structural interrelationships defined between ears 116 and bar 118 of the cable housings 68 and 108. A catch or clasp housing 140, which is somewhat similar to housing 120, is adapted to be removably secured upon bridge bar 136, and in order to accomplish the same, it is seen, from FIGS. 2 and 2A, that housing 140 is provided with a rectangular slot 142, as viewed in elevation or cross-section, within the lower portion thereof and is also provided with a substantially L-shaped slot 144 within the upper portion thereof when similarly viewed.

The entire thickness or depth of housing 140 is substantially the same as that of housing section 14, and the depth of slot 142 is approximately one-half that of housing 140 or housing 14 and is substantially the same as that of bridge bar 136. In this manner, when housing 140 is fixed upon bridge bar 136 by disposing the latter within slot 142, the forward and rear surfaces of housing 140 will be flush with or lie within the same planes as the front and rear surfaces of housing section 14. It will be further appreciated that due to the disposition of bridge bar 136 within slot 142, and therefore the interdisposition of bar 136 between lower and upper land areas 146 and 148 of housing 140 which serve to define slot 142, when housing 140 is mounted upon housing section 14 in the foregoing manner, and housing sections 12 and 14 are in turn mated together, housing 140 will be fixedly secured within the housing assembly comprising sections 12 and 14.

Prior to the mounting of the device upon a patient, and with the components of the device disposed in the illustrated position, clasp housing 140 will be initially mounted upon housing section 14 in the manner previously described, and housing section 12 will then be mated with housing section 14. The housing assembly 12-14, that is, the device per se, will then be positioned upon the central chest area of the patient and over any undergarments worn by the patient, and with the harness cable 104 initially extending across the right portion of the patient's chest and about the right lateral side of the patient's body and across the back portion thereof, cable housing 108 and cable 104 will be disposed about the left lateral side of the patient and across the left portion of the patient's chest so as to dispose the catch bar 118 of cable housing 108 within slot 112 of catch housing 120 and to engage bar 118 with the hooked portion 124 of housing 120.

As cable 104 is freely movable within and relative to housing 107, the latter may be adjustably positioned with respect to and upon cable 104 so as to be disposed within the laterally central portion of the patient's back, or in other words, within the vicinity of the spinal column. In this manner, harness 114 will be properly positioned such that a binding portion 150, which serves to define an endless loop portion 152 within harness 114, will be properly positioned at the base of the patient's neck within the upper back or scapula region of the patient's body. Loop portion 152 of harness 114 will then be able to be disposed over the patient's head whereby the free, closed end 154 will be able to be operatively disposed within slot 144 of housing 140 and be operatively engaged with hooked portion 156 of the housing 140, while such an assembly, and the device 10, is supported by means of the patient's neck and scapula region through means of the bound portion 150 of harness 114. Lastly, harness cable 64 is extended downwardly along the front laterally central region of the patient's body and about the pubis area thereof so as to extend upwardly along the dorsal, laterally central region of the body whereby catch bar 118 of cable housing 68 will be able to be disposed within slot 130 of catch housing 107 so as to interengage bar 118 with the hooked portion of housing 107 defining slot 130 in the same manner as bar 118 of housing 108 engaged hooked portion 124 of housing 120.

It will of course be further appreciated from the foregoing that depending upon the size of the patient, the lengths of harness cables 64 and 104 may be adjusted through means of the adjustable reel structure of cable housings 68 and 108, and in fact, the length of cable 64 is adjusted such that sufficient tension is impressed thereon and transmitted to the slidable plate assembly 24-36 and the spring-biased reel assemblies 52-54 whereby the upper surface 158 of plate 24 will be disposed at a predetermined position which is located a distance from upper stop member 58 which is approximately equal to one-half of the entire stroke of the plate assembly 24-36, which stroke is of course defined by the distance between the lower surface 160 of plate 24 and lower stop member 60. This position of plate 24 will serve to properly locate plate 36 relative to the lateral transverse plane of movement of contact plate 84 and terminal contact 96 such that when plates 24 and 36 are in the aforenoted position, which corresponds to the operational position of the same when the patient has achieved a correct postural position or condition, contact member 96 will be in contact with section 38 of conductive plate 36, and at an approximate position thereof as indicated at 162, or in other words, within the right vertically central portion of section 38, that is, near the right edge of plate section 38, as viewed in FIG. 1, and substantially centrally between the upper edge thereof and the lowermost, corner portion thereof.

The conductive plate 36 and its contact members 44 and 46, as well as plate 84 and its contact member 96, together form an electrical assembly which may be likened to a single-pole, double-throw switch, with contact member 96 serving as the common contact. A pair of contacts or brushes 164 are disposed within a transverse plane of housing section 14 which corresponds to a similar plane containing reels 52 and 54, and it will be appreciated that contacts are cantilevered with respect to housing section 14, one end 166 thereof being secured to section 14 by means of suitable threaded fasteners 168 while the other ends 170 thereof are freely suspended and project out of the surface plane of housing section 14 so as to in fact insure contact with reel assemblies 52 and 54.

The foregoing electrical components are all disposed within conventional integrated electrical circuitry which includes a suitable tone, alarm, or vibrator signal means, not shown, which, as noted heretofore, is provided for indicating when actuated, to the patient, that an incorrect postural position or condition has been assumed. The integrated circuitry is of the Mos/Fet type and the use of such integrated circuitry is particularly advantageous in view of the fact that the non-operational current flow is virtually zero which results in a considerable conservation in battery life.

In order to furnish an index of how well the patient is succeeding or performing in overcoming the postural problems, it may be desirable to record the behavior of the patient, such as, for example, the total percentage time the patient failed to achieve the correct postural condition within which time period the alarm or tone device was activated, and such has been accomplished through the provision of an electrolytic timer 172 which may be mounted, by suitable fasteners, not shown, upon mounting plate 60 of housing section 12. Timer 172 has male plug elements 174 which may be mated with a female plug fitting 176 mounted upon the bottom surface 178 of housing section 14, it of course also being appreciated that such elements are incorporated within the electrical circuitry of the device which is housed within housing section 14.

In operation, when the device is mounted upon the patient's chest in the aforenoted manner, and assuming, for example, an initial correct postural position of the patient, plate 36 will be disposed in the position heretofore described and somewhat below that illustrated in FIG. 1, and plate 84 and its contact member 96 will be dispoed within its transverse plane such that movement of the same within such plane, due to respiration of the patient will move contact member 96 relative to plate 36. Consequently, for substantially all degrees or depths of respiration, contact member 96 will be disposed solely within plate section 38, it being remembered that along with the movement of contact member 96 across plate 36 from the right toward the left, as viewed in FIG. 1, there is a simultaneous downward movement of plate 36 due to the lengthening of cable 64 also as a result of such respiration, whereby the tone, alarm, or vibrator circuitry will not be actuated as contact between member 96 and plate section 38 corresponds to an open circuit condition.

However, should the patient assume a poor or incorrect postural position or condition, then the length of cable 64 will be shortened due to the slouching of the patient, and consequently, the spring biased mechanisms operatively associated with reels 52 and 54 will tend to rewind chains or cables 48 and 50 and thereby raise plate assembly 24-36 upwardly. This of course alters the position of contact member 96 relatively downwardly with respect to plate 36 and sections 38 and 40, and in fact causes member 96 to traverse gap 42 of plate 36 and to enter zone 40 of plate 36 which, together with contact member 96 corresponds to a closed circuit condition and thereby activates the tone circuitry so as to indicate to the patient that he or she has in fact achieved an incorrect or poor postural positional or condition.

It will thus be apparent that through the provision of gap 42, wherein the same has the particularly defined curvature or rectilinear slope, as well as the provision of transversely movable plate 84 and its contact member 96 which reflects the degrees or depths of respiration of the patient, the fact that the length of cable 64 may be lengthened otherwise than by attaining a good postural position, that is, by deep respiration activity, which therefore would normally give an erroneous indication of a proper postural position, such is automatically compensated for whereby a true indication of a proper or correct postural condition or position is in fact achieved. In other words, an appropriate fraction of the length or lengthening of the cable 64 is automatically subtracted from the total length or elongation of such cable, which fraction represents the lengthening due to respiration, whereby a true indication of such cable length is obtained so as to activate or render inoperative the tone or alarm circuitry. In this manner, the underlying curvature of the spinal column, which is defined as the difference in the distance or length between the cervical vertebra C7 and the pubis, and the total length of the spinal column, is in fact monitored and treated in a physically therapeutic corrective manner.

It will be further noted that the gap 42 does not fully extend up to the upper left corner of plate 36 and that plate 40 includes a longitudinally projecting elongated section 180. The purpose of this section of closed-circuit plate 40 is to prevent the patient from overriding the system by exceptionally deep respiration. It can be appreciated from FIG. 1 that if gap 42 were continued in its curved or rectilinear fashion until the same encountered the left lateral edge of plate section 40, then upon deep respiration by the patient, contact member 96 would be disposed within the extreme left portion of plate 36, as viewed in FIG. 1, due to the extension of cable 104, however, plate 36 would also be disposed within the lower portion of recess 20 due to the simultaneous extension of cable 64. Consequently, contact member 96 could forseeably be disposed within the upper left portion of open-circuit 38, even if the patient were to slouch to a considerable degree, whereby no indication of the same would be given. With the provision of section 180 of plate section 40, however, the system cannot be overridden despite any degree of respiration.

Figure 4:
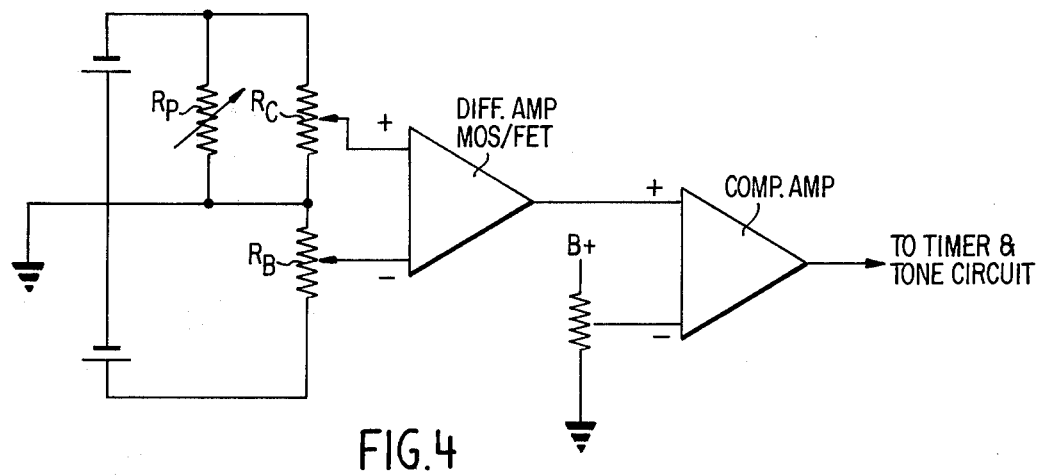
FIG. 4 is a schematic circuit diagram characteristic of the embodiment of the posture training device of the present invention disclosed in FIG. 3.

Considering next the embodiment of FIGS. 3 and 4, in lieu of the mechanical, sliding-plate type system of the embodiment of FIGS. 1 and 2, the embodiment of FIGS. 3 and 4 employs two film deposited rotary potentiometers 200 and 202 which are respectively connected to a body cable 204 which extends about the longitudinal axis of the body from the pubis to the scapula and corresponds to cable 64 of the first embodiment, and a chest cable 206 which extends laterally about the upper torso of the body and corresponds to cable 104. As best seen from the schematic illustration of potentiometer 202 of FIG. 3, each of the potentiometers includes a low resistance track or resistive substrate 208, which is electrically connected to the other circuit elements, and a rotary double wiper contact element 210 which engages a track or substrate 208 and which is built into a watch-spring return mechanism, not shown, which may be the same as those employed in the mechanical embodiment of FIGS. 1 and 2, and which are of course operatively connected to cables 204 and 206.

The potentiometers may be conventional, such as, for example, of the type manufactured by the Markite Division of Litton Industries. It will be appreciated that as a result of the foregoing structure, the length change in both the chest and body cables are converted into appropriate resistance values, which may be diagrammatically indicated as $R_B$ and $R_C$, respectively, such values hereinafter diagrammatically representing potentiometers 200 and 202, respectively, and the voltage values, which are then generated by the potentiometer circuits, are then seen to be proportional to the cable lengths. It is to be additionally noted that in the embodiment of FIG. 3, both cable mechanisms are rotatably supported within a single housing section, as opposed to the structure of the first embodiment of FIGS. 1 and 2 wherein the body cable 64 was, for example, rotatably supported within housing section 12 while chest cable 104 was similarly supported within housing section 14.

With reference now being made more particularly to FIG. 4, the potentiometers $R_B$ and $R_C$ are seen to be disposed within an analog computation circuit and it will be additionally noted that a trim resistor $R_p$ is disposed in a parallel relationship with potentiometer $R_C$ so as to serve a trimming function with respect to potentiometer $R_C$. Such a trimming function corresponds to the provision of the curved or sloped, linear gap 42 of the mechanical embodiment, whereby the voltage values of the potentiometers $R_B$ and $R_C$ are thus properly interrelated so as to compensate for or accommodate the increased cable length in body cable 204 which is due to respiration so as to in fact achieve a true or uncontaminated index of the cable length from the pubis to the scapula which of course indicates whether or not a correct or incorrect postural condition or position, or underlying curvature of the spinal column is being achieved.

After the relative voltage values of the potentiometers are so scaled or trimmed, the same are applied to a differential amplifier of the M*os/F*et type, and the amplified difference value is then applied to a comparator circuit or amplifier, such as, for example, a Schmitt trigger, which then issues an appropriate signal to the tone or alarm circuitry which ultimately produces a signal to the patient if a poor postural position is assumed.

With respect to the time and tone circuitry, various modes of operation are of course possible with either of the embodiments of the present invention. For example, a simple time delay may be programmed into the circuitry, and this is seen to be quite advantageous and desirable. In accordance therewith, after the electrical circuitry associated with the device is activated to its ON state as a result of the patient assuming a poor postural condition, there is a predetermined, adjustable delay period or time interval before the tone or alarm signal is actually emitted. This permits the patient to intentionally assume a position which might otherwise be considered one of poor posture in order to perform certain tasks, such as, for example, picking up a ball, tying a shoe, or the like. After the predetermined time period has elapsed, then the tone or alarm signal is actually emitted. Consequently, sufficient time is allotted to permit the patient to perform the aforenoted tasks without the emission of the tone or alarm, however, if the time period elapses, which would probably inidcate that an unintentional poor postural position has been assumed, then the signal is emitted. Upon the resumption of a good postural position, the signal is immediately terminated, such of course serving the important punishment-reward function.

With the aforenoted timing circuit, however, it has been observed that patients could possibly effectively override the system and the therapeutic functions of the device of the present invention by assuming poor postural positions for substantially continuous periods of time with exceptionally brief periods of good postural conditions or positions interposed therebetween, such latter periods being just long enough to deactivate the tone or alarm signal. In view of such, the timing circuitry may be programmed such that the predetermined grace period, normally permitting the assumption of the poor postural condition in order to perform other tasks, can only be obtained if a good postural condition has been previously maintained for a similar time period. Still further, and alternatively, in lieu of such 1:1 ratio of the grace period: good posture period, the ratio may be programmed to be 1:2 or even higher, whereby the patient must maintain a good postural condition for a longer period of time in order to earn a predeterminedly less grace period of time.

With respect to the particular tone or alarm emitted, there are likewise variations possible. When the predetermined time period elapses at the end of which the tone or alarm is to be emitted or indicated, the tone or alarm device may be activated at its full intensity. Alternatively, however, a two-tone system may be provided, wherein a low intensity tone or alarm is initially emitted, such being just barely audible or perceivable, as in the case of a vibrator, for example, by the patient, and after another predetermined time period, if the patient has not corrected his or her postural position, a high intensity tone or signal is emitted. In this manner, the patient is motivated to be alert to assume a correct postural position, the patient being aware of the fact that if transgressions nevertheless occur he or she will not be socially embarrassed if he or she is nevertheless alert to the low intensity signal, however, if he or she is not particularly alert, the high intensity signal will assuredly be emitted. Of course, the assumption of a correct postural position at any time immediately terminates either the low or high intensity signal.

Thus, it may be seen that the posture training device of the present invention has important advantages over the known prior art devices in that the device of the present invention is readily, comfortably wearable by the patient and is seen to simply and accurately indicate whether or not a proper or improper postural position has been assumed as a result of the mechanical or electronic means of subtracting a predetermined fraction of the expansion or lengthening of the chest cable, which is due to the respiration of the patient, from the overall lengthening or expansion of the body cable which is due to both the respiration of the patient and the assumption of a correct postural position by the patient.

Obviously, many modifications and variations of the present invention are possible in light of the above teachings. It is to be understood therefore that within the scope of the appended claims the present invention may be practiced otherwise than as specifically described herein.

What is claimed as new and desired to be secured by letters patent of United States is:

1. A posture training device to be worn by a person so as to improve the person's posture, comprising:
    first harness cable means disposed about the longitudinal axis of the torso of the person and having a length which is variable depending upon a change in the posture of said person and/or a change in the underlying curvature of the spinal column, as well as upon a change in the degree of respiration of said person;
    second harness cable means disposed transversely about the upper torso of said person and having a length which is variable depending upon a change in the degree of respiration of said person;
    signal emitting means for emitting a signal when said person assumes a poor postural condition or position so as to indicate to said person the assumption of said condition or position;
    electrical control means operatively connected to said first and second harness means for controlling an electrical circuit including said signal means; and
    means for correlating the changes in length of said first and second cable means such that said electrical control means will activate or deactivate said signal means only when the change in length in said first cable is due to a change in the posture and/or underlying curvature of the spinal column of said person.

2. A posture training device as set forth in claim 1, wherein said electrical control means comprises:
    an electrically conductive plate, having two separate contact zones insulated from each other by a gap, operatively connected to said first harness cable; and
    a contact member operatively connected to said second harness cable;
    said plate and contact member establishing a single-pole, double throw switch assembly.

3. A posture training as set forth in claim 2, wherein: said plate is slidably disposed in the longitudinal direction upon a first section of a housing of said device; and
    said contact member is slidably disposed in the transverse direction upon a second section of said housing which is adapted to mate with said first section; whereby the sliding movements of said plate and contact member determine the relative disposition of said contact member relative to said contact zones of said plate so as to control said circuit.

4. A posture training device as set forth in claim 1, further comprising:
    spring biasing means operatively connected to said first and second cable means,
    whereby said lengths of said first and second cables are rendered variable against the biasing forces of said spring means.

5. A posture training device as set forth in claim 4, wherein:
    said spring means are isotonic,
    whereby the expansion or contraction of said first and second cables is independent of the displacement of the same from a predetermined position.

6. A posture training device as set forth in claim 3, wherein said correlating means comprises:
    said gap being rectilinearly configured and disposed at a predetermined slope or angle with respect to a horizontal plane.

7. A posture training device as set forth in claim 6, wherein:
    said slope or angle is approximately 34°.

8. A posture training device as set forth in claim 1, further comprising:
    means for fixedly adjusting the length of said cables so as to adapt said device to different sized persons.

9. A posture training device as set forth in claim 1, wherein:
    said signal means is a tone device.

10. A posture training device as set forth in claim 1, further comprising:
    timer means disposed in said circuit for indicating the accumulative time said person is in a poor postural condition.

11. A posture training device as set forth in claim 10, wherein:
    said timer means is an electrolytic timer.

12. A posture training device as set forth in claim 1, wherein said electrical control means comprises:
    a rotary potentiometer operatively connected to each one of said first and second cables;
    a differential amplifier electrically connected to said potentiometers; and
    a comparative amplifier electrically connected to said differential amplifier.

13. A posture training device as set forth in claim 11, wherein:
    said correlating means comprises a trim resistor.

14. A posture training device as set forth in claim 1, wherein:
    said signal means is a vibrator device.

15. A posture improving device comprising:
    a body harness whose length changes in correspondence with body height changes;
    attached means for subtracting out the component of body height due to breathing from that due to posture changes;
    switching means actuatable by said harness at a predetermined body height as determined by said harness; and
    an alarm means actuatable by said actuated switching means;
    said alarm means comprises a two level system, the lower of which is actuated when poor posture is first detected by said harness, and the upper one of which is activated after a predetermined time period in which said poor posture remains uncorrected.

* * * * *